United States Patent
Tonomura et al.

(10) Patent No.: US 6,359,161 B2
(45) Date of Patent: Mar. 19, 2002

(54) PREPARATION OF HALOPROPYLDIMETHYLCHLOROSILANES

(75) Inventors: Yoichi Tonomura; Tohru Kubota; Mikio Endo, all of Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/852,638

(22) Filed: May 11, 2001

(30) Foreign Application Priority Data

May 15, 2000 (JP) .................................. 2000-142128

(51) Int. Cl.⁷ .................................................. C07F 7/08
(52) U.S. Cl. ....................................................... 556/479
(58) Field of Search ......................................... 556/479

(56) References Cited

U.S. PATENT DOCUMENTS 4,658,050 A * 4/1987 Quirk et al. ................ 556/479
5,616,762 A * 4/1997 Kropfgans et al. ......... 556/479
6,153,782 A * 11/2000 Krauter et al. .............. 556/479
6,177,585 B1 * 1/2001 Chewn et al. ............... 556/479

FOREIGN PATENT DOCUMENTS

JP      2938731      6/1999

OTHER PUBLICATIONS

English abstract of JP 2,938,731, 1999.

* cited by examiner

*Primary Examiner*—Paul F. Shaver
(74) *Attorney, Agent, or Firm*—Millen, White, Zelano & Branigan, P.C.

(57) ABSTRACT

A halopropyldimethylchlorosilane is prepared by reacting dimethylchlorosilane with an allyl halide in the presence of an iridium catalyst. The reaction is effected in the presence of an internal olefin compound, typically 1,5-cyclooctadiene. The internal olefin compound suppresses deactivation of the iridium catalyst during reaction. Using a smaller amount of the iridium catalyst, the process produces the halopropyldimethylchlorosilane in high yields.

3 Claims, No Drawings

PREPARATION OF HALOPROPYLDIMETHYLCHLOROSILANES

This invention relates to a process for preparing halopropyldimethylchlorosilanes which are useful as intermediates for the synthesis of various silane coupling agents and as modifiers for silicone fluid.

BACKGROUND OF THE INVENTION

Halopropylchlorosilane compounds are used as intermediates for the synthesis of various silane coupling agents and as modifiers for silicone fluid. These compounds are generally synthesized by reacting allyl halides with hydrogenchlorosilane compounds such as trichlorosilane, methyldichlorosilane and dimethylchlorosilane. In the reaction, platinum and rhodium-containing compounds are used as the catalyst.

The process of preparing halopropylchlorosilane compounds using platinum-containing compounds is disclosed, for example, in U.S. Pat. Nos. 2,823,218, 3,814,730, 3,715,334, 3,516,946, 3,474,123, 3,419,593, 3,220,922, 3,188,299, 3,178,464, and 3,159,601. The process using rhodium-containing compounds is disclosed, for example, in U.S. Pat. Nos. 3,296,291 and 3,564,266. Most of these processes use trichlorosilane and methyldichlorosilane as the hydrogenchlorosilane compound.

The use of trichlorosilane and methyldichlorosilane as the hydrogenchlorosilane compound is described in many patents as noted above. However, the use of dimethylchlorosilane is described in few patents because of low selectivity of reaction, although the end products, halopropyldimethylchlorosilane compounds are useful as intermediates for the synthesis of various silane coupling agents and as modifiers for silicone fluid. The only known process is Japanese Patent No. 2938731 directed to the preparation of a halopropyldimethylchlorosilane compound using an iridium complex. This process, however, suffers from the problem that a large amount of the expensive iridium complex must be used as the catalyst, and is thus not regarded as advantageous in practicing on an industrial scale.

SUMMARY OF THE INVENTION

An object of the invention is to provide a simple process for preparing halopropyldimethylchlorosilanes on an industrial scale.

The invention pertains to a process for preparing a halopropyldimethylchlorosilane of the following general formula (1):

$$XCH_2CH_2CH_2Si(CH_3)_2Cl \qquad (1)$$

wherein X is chlorine, bromine or iodine, by reacting dimethylchlorosilane with an allyl halide of the following general formula (2):

$$XCH_2CH=CH_2 \qquad (2)$$

wherein X is as defined above in the presence of an iridium catalyst. Quite unexpectedly, the inventor has found that deactivation of the iridium catalyst during reaction is suppressed by adding an internal olefin compound of the following general formula (3) to the reaction system.

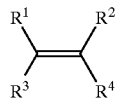

Herein $R^1$ and $R^2$ each are a monovalent hydrocarbon group having 1 to 10 carbon atoms, or $R^1$ and $R^2$ may together form a ring, $R^3$ and $R^4$ each are hydrogen or a monovalent hydrocarbon group having 1 to 10 carbon atoms. Even when the amount of the iridium catalyst used is reduced, the halopropyl-dimethylchlorosilane is produced in high yields.

The invention provides a process for preparing a halopropyldimethylchlorosilane of the general formula (1):

$$XCH_2CH_2CH_2Si(CH_3)_2Cl \qquad (1)$$

reacting dimethylchlorosilane with an allyl halide of the general formula (2):

$$XCH_2CH=CH_2 \qquad (2)$$

in the presence of an iridium catalyst, characterized in that the reaction is effected in the presence of a compound of the general formula (3):

Herein, X and $R^1$ to $R^4$ are as defined above.

DESCRIPTION OF THE PREFERRED EMBODIMENT

The starting reactant to be reacted with dimethylchlorosilane is an allyl halide of the general formula (2):

$$XCH_2CH=CH_2 \qquad (2)$$

wherein X is chlorine, bromine or iodine. Specifically, the allyl halides are allyl chloride, allyl bromide and allyl iodide. The amount of the allyl halide used is not critical although it is preferred to use 0.5 to 2.0 mol, especially 0.9 to 1.2 mol of allyl halide per mol of dimethylchlorosilane.

The iridium catalyst used herein encompasses iridium salts and iridium complexes. Exemplary iridium salts are iridium trichloride, iridium tetrachloride, chloroiridic acid, sodium chloroiridate and potassium chloroiridate. The iridium complexes include those represented by the following general formula (4):

$$[Ir(R)Y]_2 \qquad (4)$$

wherein R is a diene compound and Y is chlorine, bromine or iodine. Illustrative examples of the iridium complexes of formula (4) include di-μ-chlorobis(μ-1,5-hexadiene)diiridium, di-μ-bromobis(μ-1,5-hexadiene)diiridium, di-μ-iodobis(μ-1,5-hexadiene)diiridium, di-μ-chlorobis(μ-1,5cyclooctadiene)diiridium, di-μ-bromobis(μ-1,5-cyclooctadiene)diiridium, di-μ-iodobis(μ-1,5-cyclooctadiene)diiridium, di-μ-chlorobis(μ-2,5-norbornadiene)diiridium, di-μ-bromobis(μ-2,5-norbornadiene)diiridium, and di-μ-iodobis(μ-2,5,-norbornadiene)diiridium.

No particular limit is imposed on the blending ratio of the iridium catalyst although it is preferred to use the iridium catalyst in such amounts as to give 0.000001 to 0.01 mol, especially 0.00001 to 0.001 mol of iridium atom per mol of dimethylchlorosilane. Less than 0.000001 mol of the catalyst may fail to exert catalytic effects whereas more than 0.01 mol of the catalyst may not provide reaction promoting effects corresponding to the increment of the catalyst.

According to the invention, the reaction of dimethylchlorosilane with the allyl halide of formula (2) is carried out in the presence of not only the iridium catalyst, but also an internal olefin compound of the formula (3).

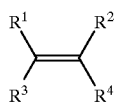
(3)

Herein $R^1$ and $R^2$ each are a monovalent hydrocarbon group having 1 to 10 carbon atoms, or $R^1$ and $R^2$, taken together, may form a ring. $R^3$ and $R^4$ each are hydrogen or a monovalent hydrocarbon group having 1 to 10 carbon atoms. Illustrative examples of the compound of formula (3) include 2-hexene, 3-hexene, 2-heptene, 2-octene, 4-octene, 2-decene, 5-decene, cyclopentene, cyclohexene, 2-norbornene, 1,3-cyclohexadiene, 1,4-cyclohexadiene, 4-vinyl-1-cyclohexene, 1,5-cyclooctadiene, 2,5-norbornadiene, 5-vinyl-2-norbornene, and limonene. From the reactivity and catalyst stability standpoints, 1,5-cyclooctadiene is most preferred.

No particular limit is imposed on the amount of the compound of formula (3) used although it is preferred to use 0.5 to 10,000 mol, especially 1 to 1,000 mol of the compound per mol of iridium atom in the iridium catalyst. Less than 0.5 mol of the compound may fail to exert the desired effects whereas more than 10,000 mol of the compound may fail to provide effects corresponding to that amount and cause more by-products to form, resulting in reduced yield and purity.

The reaction will proceed in a solventless system although a solvent is used if desired. Useful solvents include hydrocarbon solvents such as pentane, hexane, cyclohexane, heptane, octane, isooctane, benzene, toluene, and xylene; ether solvents such as diethyl ether, tetrahydrofuran, and dioxane; ester solvents such as ethyl acetate and butyl acetate; aprotic polar solvents such as acetonitrile; and chlorinated hydrocarbon solvents such as dichloromethane and chloroform, which may be used alone or in admixture of two or more.

The reaction temperature is not critical. A temperature in the range of about 0° C. to about 200° C., especially about 10° C. to about 100° C. is preferred when reaction is effected under atmospheric pressure or under pressure. The reaction time is usually from about 1 hour to about 10 hours.

According to the invention, the above-described reaction yields a halopropyldimethylchlorosilane of the general formula (1):

XCH$_2$CH$_2$CH$_2$Si(CH$_3$)$_2$Cl (1)

wherein X is chlorine, bromine or iodine. Specifically, the silanes are 3-chloropropyldimethylchlorosilane, 3-bromopropyldimethylchlorosilane, and 3-iodopropyldimethyl-chlorosilane.

EXAMPLE

Examples of the invention are given below by way of illustration and not by way of limitation.

EXAMPLE 1

A flask equipped with a stirrer, reflux condenser, dropping funnel and thermometer was charged with 153.0 g (2.0 mol) of allyl chloride, 67.2 mg (0.0001 mol) of di-μ-chlorobis(μ-1,5-cyclooctadiene)diiridium, and 0.43 g (0.004 mol) of 1,5-cyclooctadiene and heated at 35° C. Once the internal temperature was stabilized, 189.2 g (2.0 mol) of dimethylchlorosilane was added dropwise over 6 hours. During the dropwise addition, the reaction mixture continued to be exothermic. After the completion of dropwise addition, the reaction solution was stirred for one hour at 40° C. The reaction solution was distilled, collecting 317.2 g of a fraction having a boiling point of 84° C./6.7 kPa, which was 3-chloropropyldimethylchlorosilane (yield 92.7%).

EXAMPLE 2

A flask equipped with a stirrer, reflux condenser, dropping funnel and thermometer was charged with 153.0 g (2.0 mol) of allyl chloride, 67.2 mg (0.0001 mol) of di-μ-chlorobis(μ-1,5-cyclooctadiene)diiridium, and 0.33 g (0.004 mol) of cyclohexene and heated at 35° C. Once the internal temperature was stabilized, 189.2 g (2.0 mol) of dimethylchlorosilane was added dropwise over 6 hours. During the dropwise addition, the reaction mixture continued to be exothermic. After the completion of dropwise addition, the reaction solution was stirred for one hour at 40° C. The reaction solution was analyzed by gas chromatography, finding a conversion of 81.5%.

Comparative Example 1

Reaction was effected as in Example 1 except that 1,5-cyclooctadiene was omitted. The reaction mixture ceased to be exothermic after approximately 50% of the predetermined amount of dimethylchlorosilane had been added dropwise. The final conversion was as low as 50.5%.

EXAMPLE 3

A flask equipped with a stirrer, reflux condenser, dropping funnel and thermometer was charged with 153.0 g (2.0 mol) of allyl chloride, 1.9 g (0.0002 mol) of a 2 wt % butanol solution of chloroiridic acid, and 2.2 g (0.02 mol) of 1,5-cyclooctadiene and heated at 35° C. Once the internal temperature was stabilized, 189.2 g (2.0 mol) of dimethylchlorosilane was added dropwise over 6 hours. During the dropwise addition, the reaction mixture continued to be exothermic. After the completion of dropwise addition, the reaction solution was stirred for one hour at 40° C. The reaction solution was analyzed by gas chromatography, finding a conversion of 73.9%.

Comparative Example 2

Reaction was effected as in Example 3 except that 1,5-cyclooctadiene was omitted. After one hour of stirring at 40° C., the conversion was as low as 8.3%.

There has been described a process for the preparation of a halopropyldimethylchlorosilane compound from dimethyl-chlorosilane and an allyl halide in the presence of an iridium catalyst wherein an internal olefin compound is added to the reaction system for suppressing deactivation of the iridium catalyst during reaction, whereby the halopropyldimethylchlorosilane is produced in high yields despite a smaller amount of the iridium catalyst. The invention enables the efficient production of halopropyldimethylchlorosilane on an industrial scale.

Japanese Patent Application No. 2000-142128 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A process for preparing a halopropyldimethylchlorosilane of the following general formula (1):

$$XCH_2CH_2CH_2Si(CH_3)_2Cl \qquad (1)$$

wherein X is chlorine, bromine or iodine, by reacting dimethylchlorosilane with an allyl halide of the following general formula (2):

$$XCH_2CH=CH_2 \qquad (2)$$

wherein X is as defined above in the presence of an iridium catalyst, characterized in that the reaction is effected in the presence of a compound of the following general formula (3):

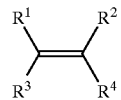

(3)

wherein $R^1$ and $R^2$ each are a monovalent hydrocarbon group having 1 to 10 carbon atoms, or $R^1$ and $R^2$ may together form a ring, $R^3$ and $R^4$ each are hydrogen or a monovalent hydrocarbon group having 1 to 10 carbon atoms.

2. The process of claim 1 wherein the iridium catalyst is a compound of the following general formula (4):

$$[Ir(R)Y]_2 \qquad (4)$$

wherein R is a diene compound, and Y is chlorine, bromine or iodine.

3. The process of claim 1 wherein the compound of formula (3) is 1,5-cyclooctadiene.

* * * * *